United States Patent
Lee et al.

(10) Patent No.: US 11,704,920 B2
(45) Date of Patent: Jul. 18, 2023

(54) METHOD FOR PROCESSING CROSS MATCHING IMAGE BASED ON DEEP LEARNING AND APPARATUS THEREOF

(71) Applicant: ARTIX Corp., Seoul (KR)

(72) Inventors: Hye Min Lee, Seoul (KR); Jung Min Lee, Seoul (KR); Jin Woo Lee, Daejeon (KR)

(73) Assignee: ARTIX Corp., Seoul (KR)

( * ) Notice: Subject to any disclaimer, the term of this patent is extended or adjusted under 35 U.S.C. 154(b) by 116 days.

(21) Appl. No.: 17/532,702

(22) Filed: Nov. 22, 2021

(65) Prior Publication Data
US 2022/0084317 A1    Mar. 17, 2022

Related U.S. Application Data

(63) Continuation of application No. PCT/KR2020/008489, filed on Jun. 29, 2020.

(30) Foreign Application Priority Data

Jun. 30, 2019 (KR) ........................ 10-2019-0078429
Jan. 16, 2020 (KR) ........................ 10-2020-0005830

(51) Int. Cl.
G06K 9/00 (2022.01)
G06V 20/69 (2022.01)
G06V 10/82 (2022.01)
G06V 10/80 (2022.01)
G06N 3/045 (2023.01)

(52) U.S. Cl.
CPC .......... *G06V 20/698* (2022.01); *G06N 3/045* (2023.01); *G06V 10/80* (2022.01); *G06V 10/82* (2022.01); *G06V 20/695* (2022.01)

(58) Field of Classification Search
None
See application file for complete search history.

(56) References Cited

U.S. PATENT DOCUMENTS

| 2005/0059095 A1 | 3/2005 | Yang et al. |
| 2006/0014135 A1 | 1/2006 | Fan et al. |
| 2010/0254589 A1 | 10/2010 | Gallagher |
| 2017/0082619 A1 | 3/2017 | Shih et al. |
| 2019/0384047 A1 * | 12/2019 | Johnson ................... G06N 3/08 |

FOREIGN PATENT DOCUMENTS

WO   2018/229490 A1   12/2018

OTHER PUBLICATIONS

Office Action issued in KR 10-2020-0005830; mailed by the Korean Intellectual Patent Office dated Jan. 20, 2021.
Gupta, Anindya et al., "Deep Learning in Image Cytometry: A Review"; Journal of Quantitative Cell Science; vol. 95A, pp. 366-380; Nov. 29, 2018.
Eulenberg, Philipp et al., "Reconstructing cell cycle and disease progression using deep learning"; Nature Communcations; vol. 8:463; pp. 1-6; Jul. 14, 2017.
International Search Report issued in PCT/KR2020/008489; dated Sep. 21, 2020.

* cited by examiner

*Primary Examiner* — Soo Jin Park
(74) *Attorney, Agent, or Firm* — Studebaker & Brackett PC

(57) ABSTRACT

The present disclosure relates to method and apparatus for processing cross matching image based on deep learning.

14 Claims, 12 Drawing Sheets

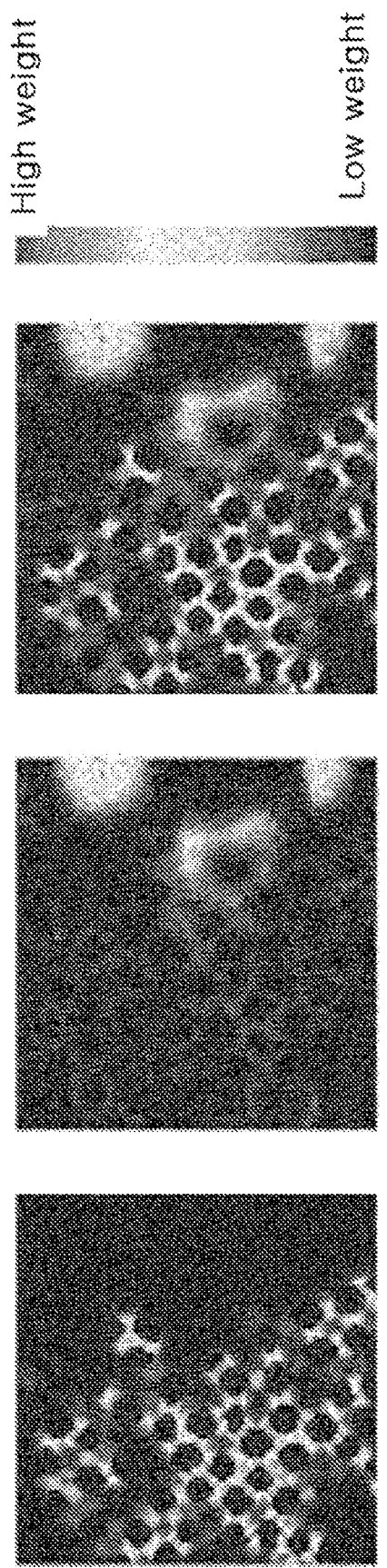

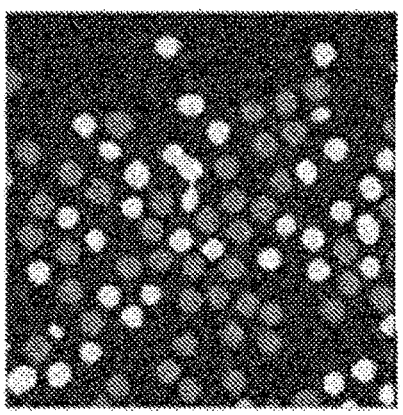
FIG. 7D UAWM applied to U-Net
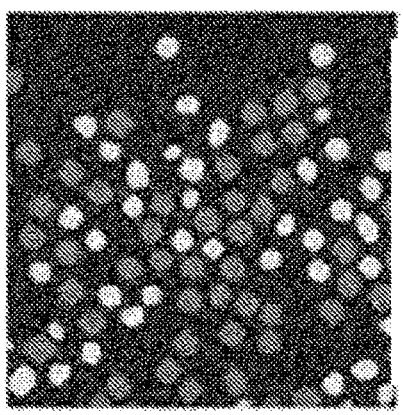
FIG. 7G UAWM applied to P-Net
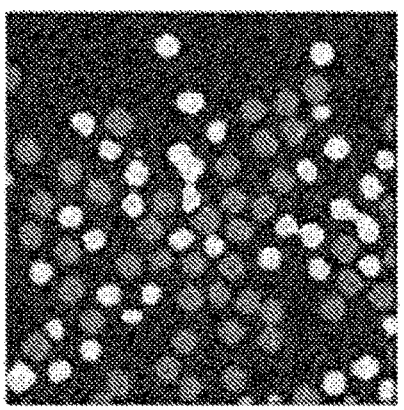
FIG. 7C DWM applied to U-Net
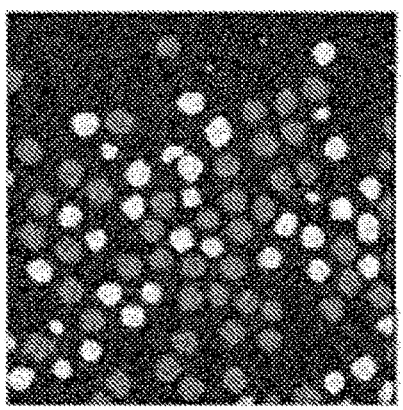
FIG. 7F DWM applied to P-Net
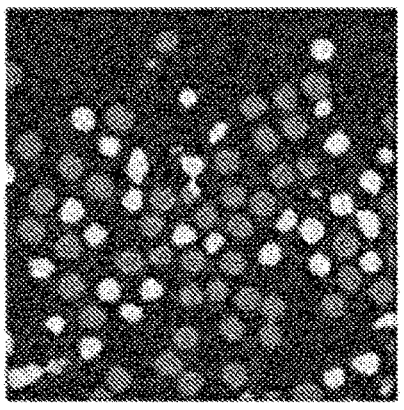
FIG. 7B UWM applied to U-Net
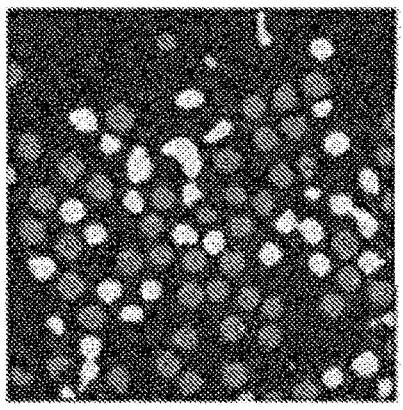
FIG. 7E UWM applied to P-Net
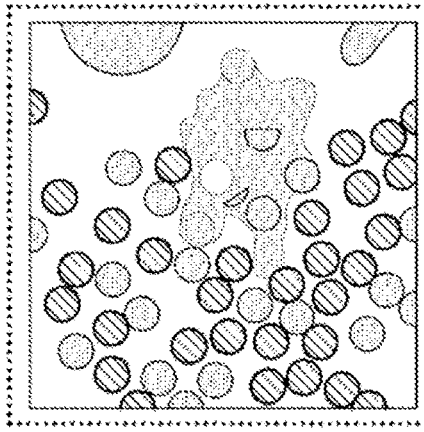
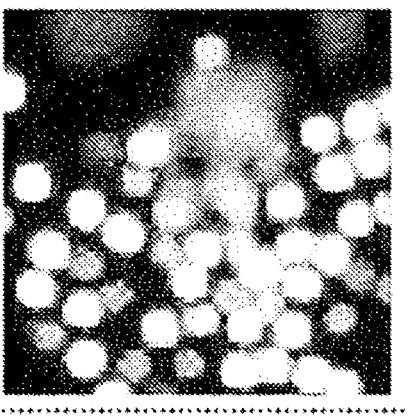
FIG. 7A Exemplary image

METHOD FOR PROCESSING CROSS MATCHING IMAGE BASED ON DEEP LEARNING AND APPARATUS THEREOF

CROSS-REFERENCE TO RELATED APPLICATION

The present application is a continuation of International Patent Application No. PCT/KR2020/008489, filed on Jun. 29, 2020, which is based upon and claims the benefit of priority to Korean Patent Application Nos. 10-2019-0078429 filed on Jun. 30, 2019 and 10-2020-0005830 filed on Jan. 16, 2020. The disclosures of the above-listed applications are hereby incorporated by reference herein in their entirety.

BACKGROUND

1. Technical Field

The present disclosure relates to method and apparatus for processing cross matching image based on deep learning.

2. Description of Related Art

Organ transplant patients may be exposed to human leukocyte antigen (HLA) of another person through a blood transfusion, pregnancy, or a past organ transplant before transplantation. So, in the case of some such patients, HLA antibodies are formed, and isogenic antibodies are sometimes formed. Donor-specific antibodies (DSAs) may induce a humoral immune response in donor organs, cause an antibody mediated rejection (AMR), and lower a survival rate of a transplanted organ.

Therefore, in the case of organ transplant, an HLA antibody test for organ transplant, namely, a test to determine whether there exist specific antibodies to HLA antigens of a specific donor in a patient's serums, is essential.

HLA cross-matching for organ transplant is to evaluate at a rate of dead cells and live cells by mixing the donor's cells and the patient's serums. That is, the HLA cross-matching is performed through the steps of counting the number of dead cells and live cells, calculating a ratio of the dead cells to the live cells, and testing positive if more than 11% of cells are destroyed.

The cross-matching before transplant prevents humoral immune response and hyperacute rejection by preventing re-sensitization to donor HLA, namely, re-exposure to the same antigen.

The cross-matching is divided into complement dependent cytotoxicity (CDC) and flow cytometry (FCX). CDC is very useful to evaluate existence of DSAs and complement fixation capacity. In order to track an antibody change as a more sensitive method after a desensitization treatment, there are many efforts to detect HLA antibodies.

The complement dependent cytotoxicity (CDC) is a method of viewing cells with a fluorescence microscope, detecting a ratio of dead cells, and detecting whether there are antibodies reacting to HLA antigens based on the ratio of dead cells.

For the CDC, first, cells of a donor are reacted with serums of a grantor, and then, the complement is added in order to determine whether the cells are destroyed or not. The complement is verified in a titer before a test, and indicates dead cells using dye which is capable of dyeing only dead cells.

Moreover, the number of the dead cells may be counted using the fluorescence microscope to calculate the ratio of the dead cells. In this instance, a test may be determined to be positive if more than 11% of cells are destroyed after comparison with a voice comparison well.

However, a CDC test takes seven to eight days. Once the test starts, the test cannot be stopped during the process thereof. Furthermore, because cells to be counted are large in number, the work of counting dead cells and live cells while looking in the fluorescence microscope is not easy. Additionally, it is not easy to replace a worker with another one while counting, and there is a wide deviation in ability between a skilled worker and an unskilled worker.

Therefore, a method and an apparatus for counting dead cells and live cells in a short period of time are demanded.

The above information described in this background section is only to enhance the understanding of the background of the present disclosure and therefore it may contain information that does not form the related art that is already known to a person having ordinary skill in the field to which this technology pertains.

SUMMARY

The present disclosure has been made to solve the above-mentioned problems occurring in the prior art, and it is an object to provide a method and an apparatus which can reduce time required for cross-matching.

Another object is to process cross-matched images based on deep learning in order to easily distinguish dead cells and live cells from one another in cross-matching images.

The objects of the present disclosure are not limited to those mentioned above, and other objects not mentioned herein will be clearly understood by those skilled in the art from the following description.

To accomplish the above objects, there is provided a method for processing cross matching image based on deep learning, the method including: a preprocessing operation of combining three class areas distinguished in an original image of a cross-matching test to create a labelled image; an operation of modelling a certain area and an uncertain area of the labelled image and creating an uncertainty-aware weight map (UAWM); and an operation of creating a classification image in which live cells and dead cells are distinguished in the original image by performing P-Net learning relative to at least one among the original image, the labelled image, and the UAWM.

According to an embodiment, the preprocessing operation includes an operation of distinguishing a first class area which is a live cell area, a second class area which is a dead cell area, and a third class area which is a background area in the original image.

According to an embodiment, the certain area is a cell inner area which is divided into the live cell area and the dead cell area in the labelled image, and the uncertain area is the remaining areas excluding the certain area in the labelled image.

According to an embodiment, the UAWM creating operation includes: an operation of creating a certain area weight map by modeling the certain area; an operation of creating an uncertain area weight map by modeling the uncertain area; and an operation of creating the UAWM using the certain area weight map and the uncertain area weight map.

According to an embodiment, the UAWM creating operation weights the certain area weight map and the uncertain area weight map, and adds up the weighted certain area weight map and the weighted uncertain area weight map in order to create the UAWM.

According to an embodiment, the classification image creating operation inputs data of the first class area, data of the second class area, and data of the third class area to U-Net networks in order to perform P-Net learning.

According to an embodiment, the classification image creating operation fuses learning result values of the U-Net networks in order to create the classification image.

According to an embodiment, there is provided an apparatus for processing cross matching image based on deep learning, the apparatus including: a preprocessing unit combining three class areas distinguished in an original image of a cross-matching test to create a labelled image; an UAWM creating unit creating an uncertainty-aware weight map (UAWM) by modelling a certain area and an uncertain area of the labelled image; and a P-Net learning unit creating a classification image in which live cells and dead cells are distinguished in the original image by performing P-Net learning relative to at least one among the original image, the labelled image, and the UAWM.

According to embodiments of the present disclosure, it is easy to distinguish dead cells and live cells using cross-matching image processing based on deep learning.

Moreover, according to an embodiment, the present disclosure can reduce time required for cross-matching.

The advantages of the present disclosure are not limited to the above-mentioned advantages, and other advantages, not specifically mentioned herein, will be clearly understood by those skilled in the art from the following description.

BRIEF DESCRIPTION OF THE DRAWINGS

FIGS. 4A to 4C are views illustrating an uncertainty-aware weight map (UAWM) according to an embodiment.

FIGS. 6A to 7G are views illustrating performance of an image processing method using an UAWM and a P-Net according to an embodiment.

DETAILED DESCRIPTION

Figure 1:
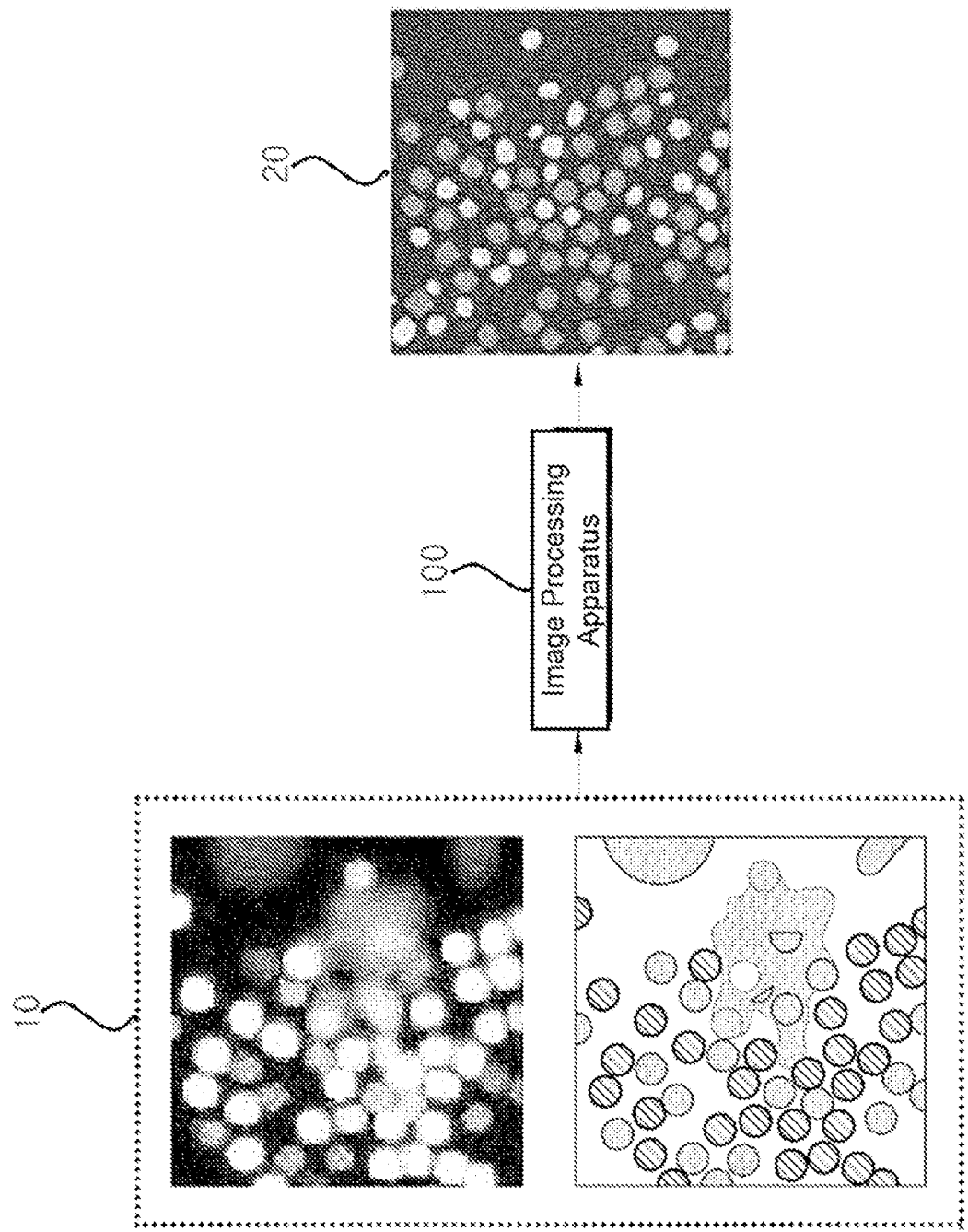
FIG. 1 is a view illustrating a cross-matching image processing environment based on deep learning according to an embodiment of the present disclosure.

Hereinafter, an embodiment will be described in detail with reference to the accompanying drawings. In the drawings, the same components have the same reference numerals. It should be noted that the following embodiments may be implemented in various different forms. It should be understood that there is no intent to limit the following embodiments to the particular forms disclosed, and on the contrary, the embodiments are intended to cover all modifications, equivalents, and alternatives falling within the technical idea and scope of the present disclosure.

Terms used in the specification are used to describe specific embodiments of the present disclosure and are not intended to limit the scope of the present disclosure. In the specification, the terms of a singular form may include plural forms unless otherwise specified. It should be also understood that the terms of 'include' or 'have' in the specification are used to mean that there are characteristics, numbers, steps, operations, components, parts, or combinations of the steps, operations, components and parts described in the specification and there is no intent to exclude existence or possibility of other characteristics, numbers, steps, operations, components, parts, or combinations of the steps, operations, components and parts.

Unless otherwise defined, all terms (including technical and scientific terms) used herein have the same meaning as commonly understood by those skilled in the technical field to which the present disclosure pertains. It will be further understood that terms, such as those defined in commonly used dictionaries, should not be interpreted in an idealized or overly formal sense unless expressly so defined herein.

Throughout the attached drawings, the same components have the same reference numerals, and repetitive descriptions thereof will be avoided. Detailed descriptions of known relevant art which have been deemed to make the gist of the present disclosure unnecessarily obscure will be omitted below.

FIG. 1 is a view illustrating cross-matching image processing environment based on deep learning according to an embodiment of the present disclosure.

Referring to FIG. 1, in the cross-matching image processing environment based on deep learning according to an embodiment, when an original image 10 is input to an image processing apparatus 100, the image processing apparatus 100 performs image processing based on deep learning relative to the original image 10 and outputs a classification image 20.

The original image 10 is an image acquired through cross-matching, namely, an image acquired using dye capable of dyeing live cells or dead cells after reacting cells of a donor with serums of a grantor. (In the original image 10 of FIG. 1, the upper image illustrates an actually acquired image in black and white, and the lower image illustrates a live cell area, a dead cell area, and a lysis cell area in different hatching styles.

When the original image 10 is input to the image processing apparatus 100, the image processing apparatus 100 performs image processing based on deep learning relative to the input original image 10, and creates a classification image 20.

The classification image 20 is data of an image processing result based on deep learning in order to easily distinguish live cells or dead cells.

In order to create the classification image 20, the image processing apparatus 100 preprocesses the original image 10, and creates a labelled image in which the original image 10 is expressed into three class areas. The image processing apparatus 100 classifies the original image 100 into (i) a first class area which is the live cell area, (ii) a second class area which is the dead cell area, and (iii) a third class area which is a background area, and then, creates the labelled image.

The image processing apparatus 100 creates an uncertainty-aware weight map (UAWM) using the labelled image. The image processing apparatus 100 creates certain area weight map (Wca) by modeling a certain area from the labelled image, and creates an uncertain area weight map (Wua) by modeling an uncertain area from the labelled image. Moreover, the image processing apparatus 100 creates an UAWM using the Wca and the Wua.

The image processing apparatus 100 creates a classification image 20 by performing P-Net learning relative to at least one among the original image 10, the labelled image, and the UAWM.

That is, the image processing apparatus 100 creates the classification image 20 using the UAWM, which is modeling data of the original image 10, and P-Net learning.

Hereinafter, the configuration and the function of the image processing apparatus 100 will be described in detail referring to FIGS. 2 to 11.

The image processing apparatus 100 is one among electronic devices, such as computers, ultra mobile PCs (UMPCs), workstations, net-books, personal digital assistants (PDAs), portable computers, web tablets, wireless phones, mobile phones, smartphones, and portable multimedia players, and may be one among all electronic devices capable of installing and executing cross-matching image processing applications related to the image processing apparatus 100. The electronic devices can carry out all operations for cross-matching image processing services, such as composition of a service screen, data input, data transmission and reception, and storage of data, under control of the cross-matching image processing applications.

Figure 2:
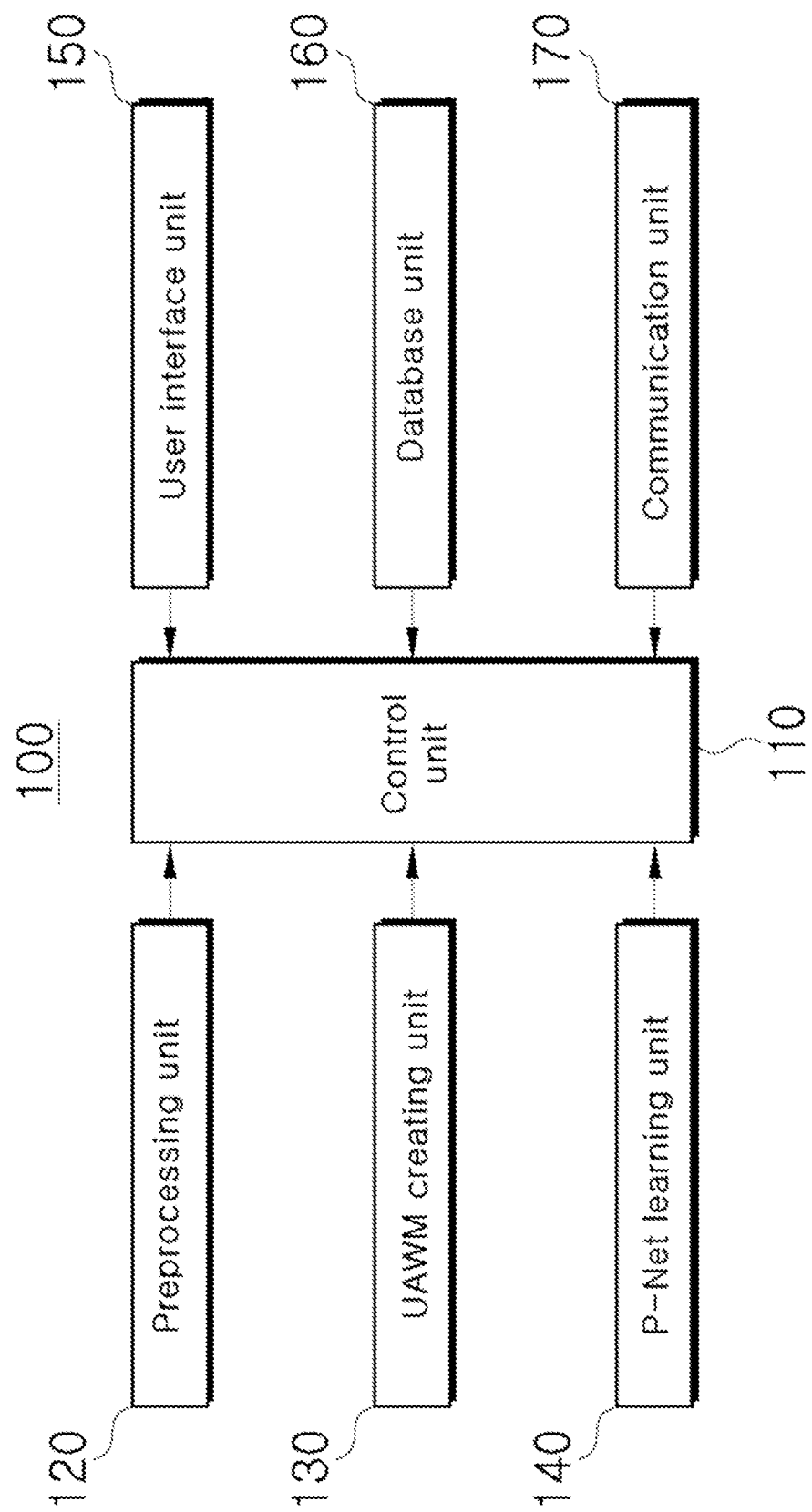
FIG. 2 is a view illustrating the configuration of an image processing apparatus according to an embodiment.

FIG. 2 is a view illustrating the configuration of an image processing apparatus according to an embodiment.

Referring to FIG. 2, the image processing apparatus 100 includes a control unit 110, a preprocessing unit 120, an UAWM creating unit 130, a P-Net learning unit 140, a user interface unit 150, a database unit 160, and a communication unit 170.

Communication among various entities included in the image processing apparatus 100 can be performed through wired/wireless network (not shown). The wired/wireless network may be standard communication technology and/or protocols.

A hardware configuration of the image processing apparatus 100 may be embodied in various manners. That is, hardware may be configured through integration of the preprocessing unit 120 and the UAWM creating unit 130 or integration of the UAWM creating unit 130 and the P-Net learning unit 140. As described above, the hardware configuration of the image processing apparatus 100 is not limited to the description of the present disclosure, and may be embodied through various methods and combinations.

The control unit 110 controls the preprocessing unit 120, the UAWM creating unit 130, the P-Net learning unit 140, the user interface unit 150, the database unit 160, and the communication unit 170 to perform various functions of the image processing apparatus 100.

Additionally, the control unit 110 may be also called a processor, a controller, a microcontroller, a microprocessor, and a microcomputer, and may be embodied through hardware, firmware, software, or combination thereof.

The preprocessing unit 120 preprocesses the original image 10, and creates a labelled image in which the original image 10 is expressed into three class areas. That is, the preprocessing unit 120 classifies the original image 100 into three class areas, and then, creates the labelled image.

First, the preprocessing unit 120 distinguishes the first class area in the original image 10. The first class area is a live cell area, and corresponds to the green color area in the original image 10 illustrated in FIG. 1, namely, the bright color area of the upper part and the diagonal hatched area of the lower part corresponding to the upper part in the original image 10.

In addition, the preprocessing unit 120 distinguishes the second class area in the original image 10. The second class area is a dead cell area, and corresponds to the orange color area in the original image 10 illustrated in FIG. 1, namely, the rounded dark color area of the upper part and the round dot-hatched area of the lower part corresponding to the upper part in the original image 10.

Moreover, the preprocessing unit 120 distinguishes the third class area in the original image 10. The third class area is a background area, and is an area excluding the first class area and the second class area. The third class area is a lysis cell area that corresponds to the blur borderline area of the upper part and the dot-hatched area of the lower part corresponding to the upper part in the original image 10, and includes the background in which cells are not arranged.

Furthermore, the preprocessing unit combines the distinguished three class areas to create a labelled image. As described above, the labelled image is an image in which the original image 10 is expressed into the three class areas.

FIGS. 3A to 3F are views illustrating images related with cross-matching according to an embodiment.

Figure 3A:
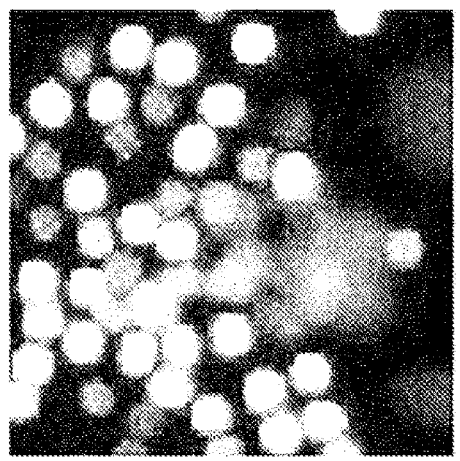
FIGS. 3A to 3F are views illustrating images related with cross-matching according to an embodiment.
Figure 3B:
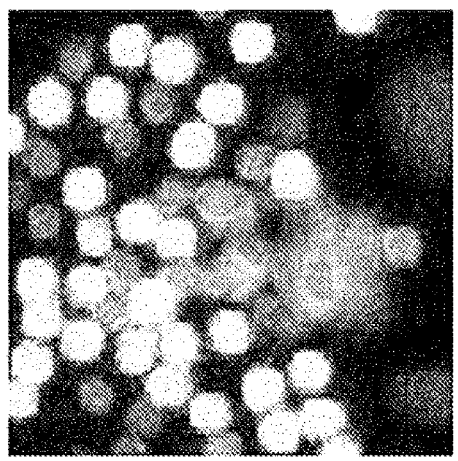
Figure 3C:
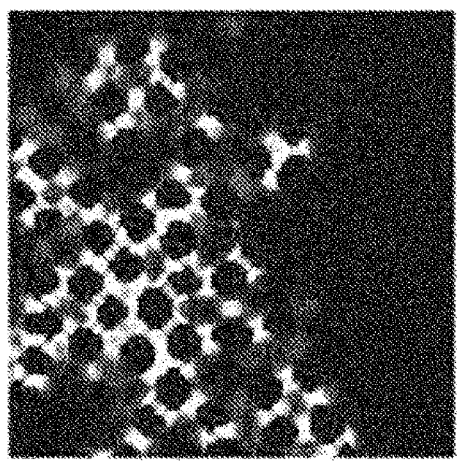
Figure 3D:
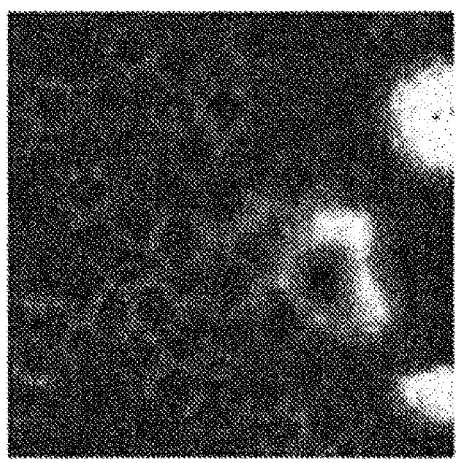
Figure 3E:
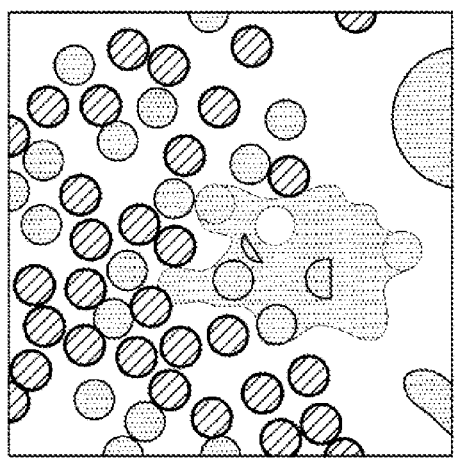

Referring to FIGS. 3A to 3F, FIG. 3A illustrates the original image 10 in black and white, FIG. 3E illustrates the live cells, the dead cells and the lysis cells in the original image 10 which are expressed in hatching styles. the green color areas in the original image 10, namely, the bright color area in FIG. 3A and the diagonal hatched area in FIG. 3E corresponding to the bright color area, are the live cell area, the clear orange color area, namely, the rounded dark color areas in FIG. 3A and the rounded dot-hatched area in FIG. 3E, are the dead cell area, and the blur orange color areas, namely, the blur borderline area in FIG. 3A and the dot-hatched area of FIG. 3E corresponding to the blur borderline area, are the lysis cell area.

Figure 3F:
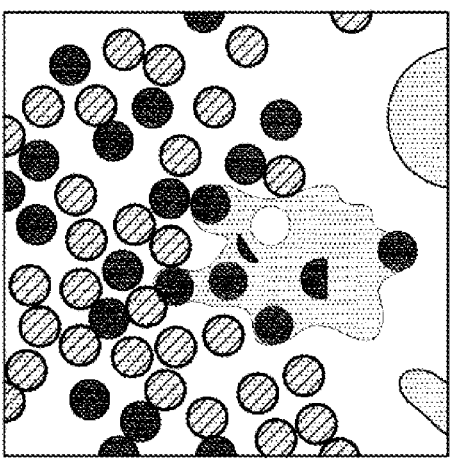

Additionally, FIGS. 3B and 3F illustrate the labelled images created through preprocessing of the original image 10 by the preprocessing unit 120. The labelled image includes (i) the first class area which is the live cell area, (ii) the second class area which is the dead cell area, and (iii) the third class area which is the background area.

Comparing the original image 10 with the labelled image, the lysis cell area of the original image 10 corresponds to the third class area which is the background area of the labelled image.

However, because the original image 10 has lots of class areas to be distinguished and the class areas are often overlapped, the preprocessing unit 120 can perform multi-task processing in order to distinguish the class areas clearly.

The UAWM creating unit 130 creates an uncertainty-aware weight map (UAWM) using the labelled image.

First, the UAWM creating unit 130 creates a certain area weight map (Wca) and an uncertain area weight map (Wua) using the labelled image.

Here, the certain area is a cell inner area which is divided into the live cell area and the dead cell area in the labelled image clearly, and the uncertain area is all remaining areas excluding the certain area in the labelled image.

In addition, the Wca is a weight map of the certain area, and has higher weight as an interval between cells gets narrower. The Wua is a weight map of the uncertain area, and models influence of the lysis cells included in the uncertain area.

The UAWM creating unit 130 creates the Wca by modeling the certain area in the labelled image, and creates the Wua by modeling the uncertain area in the labelled image.

Moreover, the UAWM creating unit 130 creates an UAWM using the Wca and the Wua.

In detail, the UAWM creating unit 130 weights the Wca and the Wua, and adds up the weighted Wca and the weighted Wua in order to create the UAWM.

Here, a mathematical formula for creating the UAWM using the Wca and the Wua can be expressed as follows:

$$w(x)=\alpha_{ca}w_{ca}(x)+\alpha_{ua}w_{ua}(x) \; s.t. \; \alpha_{ca}+\alpha_{ua}=1 \quad \text{[Mathematical formula 1]}$$

FIGS. 4A to 4C is a view illustrating an uncertainty-aware weight map (UAWM) according to an embodiment. FIG. 4A illustrates the certain area weight map (Wca), and FIG. 4B illustrates the uncertain area weight map (Wua). FIG. 4C illustrates the UAWM created through adding-up of the weighted Wca and the weighted Wua.

The P-Net learning unit 140 creates a classification image 20 by performing P-Net learning relative to at least one among the original image 10, the labelled image, and the UAWM.

Figure 5:
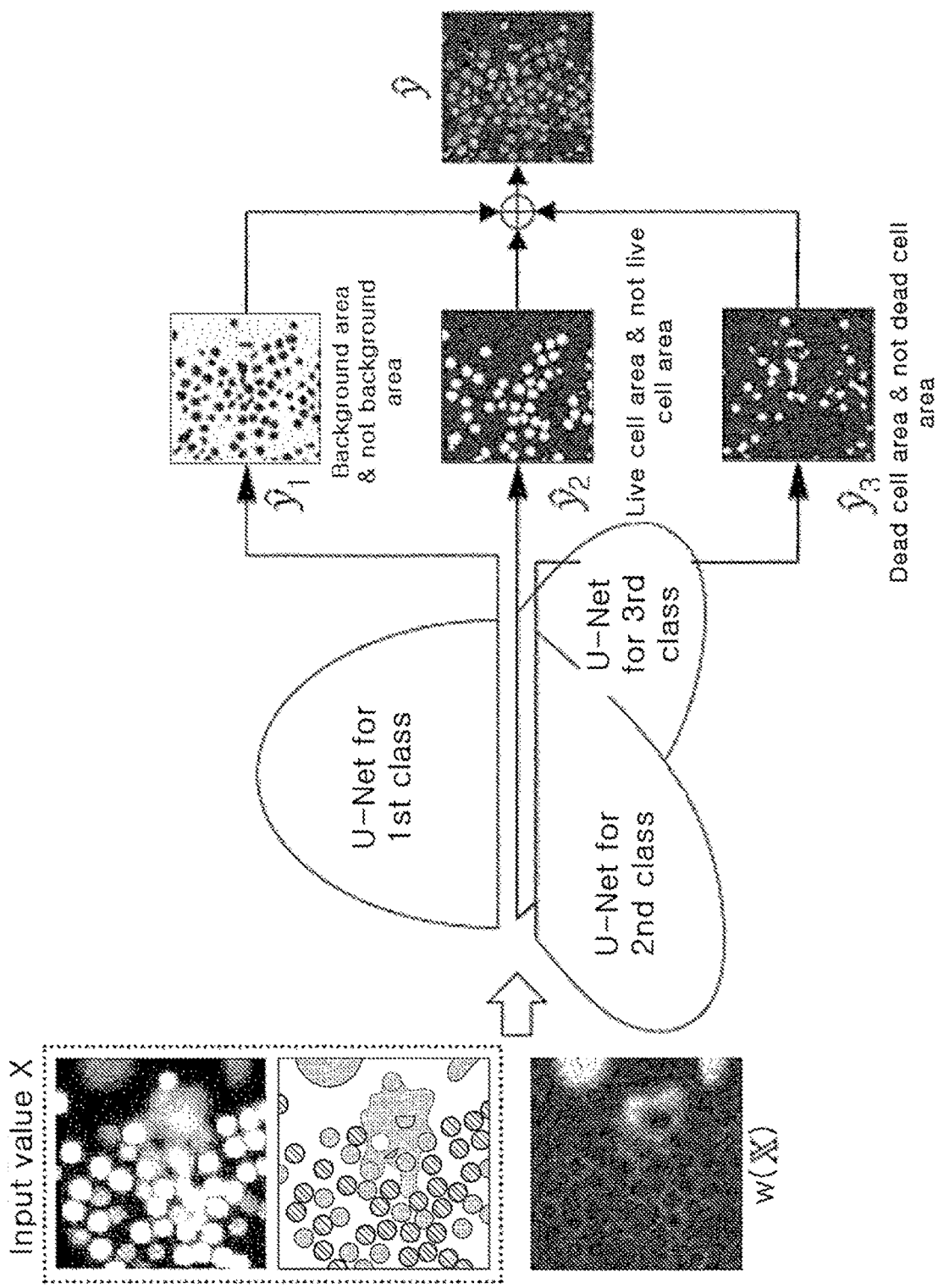
FIG. 5 is a view explaining a P-Net learning method according to an embodiment.

FIG. 5 is a view explaining a P-Net learning method according to an embodiment. Referring to FIG. 5, how to create the classification image 20 through P-Net learning by the P-Net learning unit 140 will be described.

P-Net learning is a learning method based on deep learning in order to individually segment a plurality of objects contained in input data. A P-Net includes U-Net networks configured in parallel for the purpose of deep learning of the plurality of objects.

In the P-Net learning, the plurality of objects are respectively input to the U-Net networks, and a plurality of results created through lots of U-Net learning are combined to produce the final learning data. That is, the P-Net is varied in the number of the U-Net networks according to the number of classes segmented from the input data.

The P-Net inputs the plurality of classes of the input data into the U-Net networks, and segments the plurality of classes through lots of U-Net learning. Such P-Net learning is called one-versus-all (OVA), and the OVA method of the P-Net learning is superior in terms of accuracy to learning to learn lots of classes at once.

According to an embodiment, the original image 10 which is the input data is data having three classes, namely, the live cell area, the dead cell area, and the background area. The P-Net is not to learn the three classes at once but to learn the three classes three times after respectively inputting the three classes to the U-Net networks and to add up the results.

That is, in the P-Net, the live cell area and what is not the live cell area are learned in the U-Net network for class 1, the dead cell area and what is not the dead cell area are learned in the U-Net network for class 2, and the background area and what is not the background area (live cells+dead cells) are learned in the U-Net network for class 3.

Moreover, the P-Net fuses at least one among learning result data (^y1) of the U-Net for class 1, learning result data (^y2) of the U-Net for class 2, and learning result data (^y3) of the U-Net for class 3, and creates the classification image 20 which is a P-Net learning result data (^y).

Now, how to fuse the data will be described step by step. First, the P-Net learning unit 140 inputs the first class data to the U-Net network, and creates first class classification data which is the U-Net learning result data. The first class data includes at least one among the original image 10, the labelled image in which the first class area is distinguished, and the UAWM.

Next, the P-Net learning unit 140 inputs the second class data to the U-Net network, and creates second class classification data which is the U-Net learning result data. The second class data includes at least one among the original image 10, the labelled image in which the second class area is distinguished, and the UAWM.

After that, the P-Net learning unit 140 inputs the third class data to the U-Net network, and creates third class classification data which is the U-Net learning result data. The third class data includes at least one among the original image 10, the labelled image in which the third class area is distinguished, and the UAWM.

Furthermore, the P-Net learning unit 140 fuses at least one among the first class classification data, the second class classification data, and the third class classification data, and creates the classification image 20 which is the P-Net learning result data.

The P-Net learning unit 140 performs U-Net learning independently by each class area (multiple classifiers), and then, fuses the U-Net learning result data as a conclusion. The P-Net learning unit 140 can use argmax in order to fuse at least one among the first class classification data, the second class classification data, and the third class classification data.

The user interface unit 150 provides an interface to send data to a user. The user can receive the original data 10 through the user interface unit 150.

The database unit 160 stores various data which is necessary for the image processing apparatus 100 to perform cross-matching image processing based on deep learning. For instance, the database unit 160 can store the original image 10, the labelled image, the UAWM, and the classification image 20.

The communication unit 170 performs data communication with external devices. The communication unit 170 can transfer the original image 10, the labelled image, the UAWM, and the classification image 20 to external devices.

FIGS. 6 and 7 are views illustrating performance of an image processing method using an UAWM and a P-Net according to an embodiment.

Figure 6A:
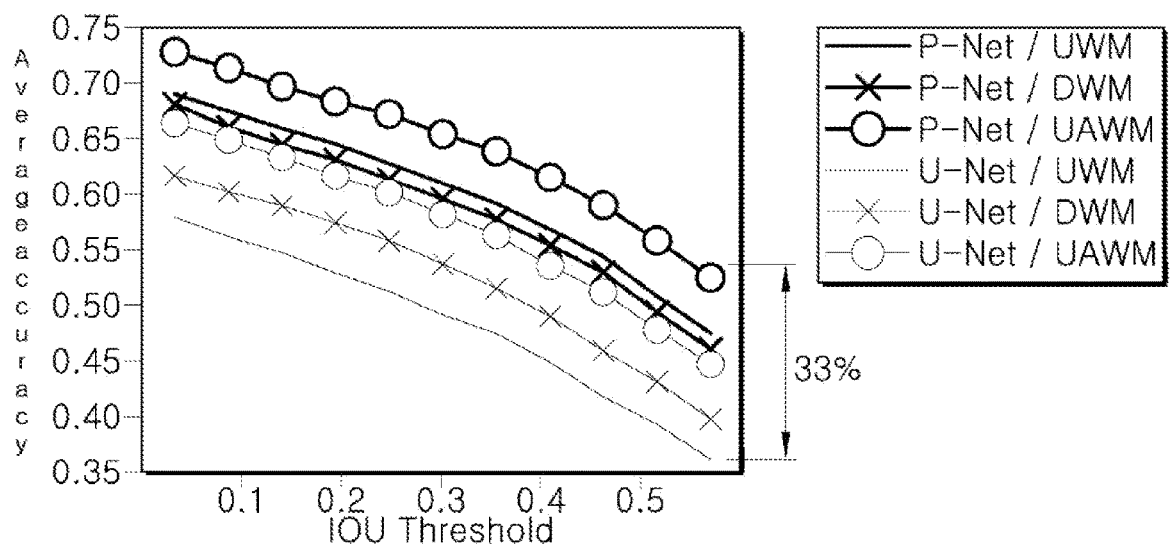
Figure 6B:
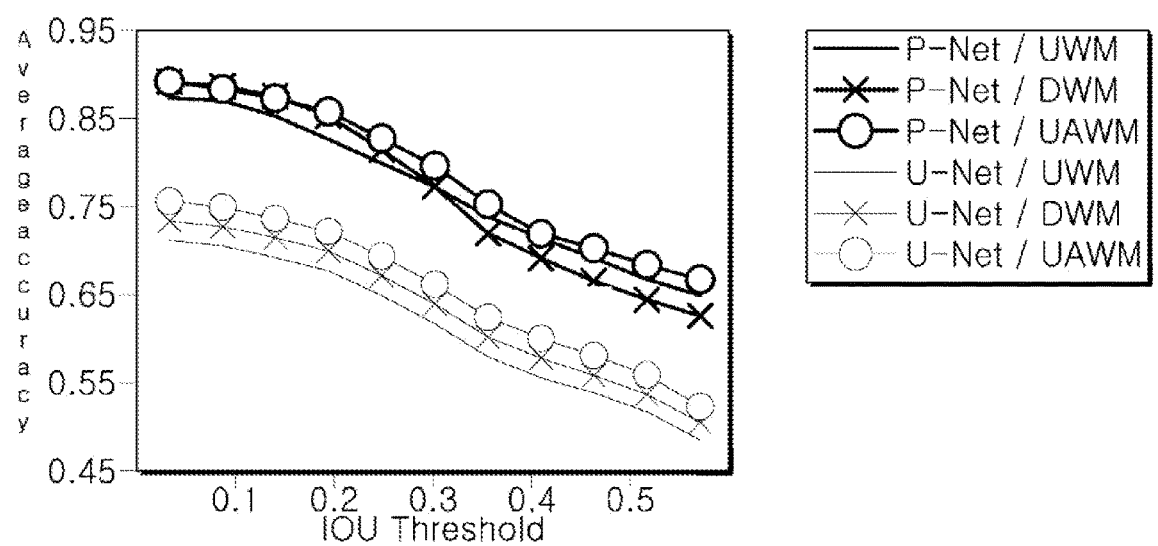
Figure 6C:
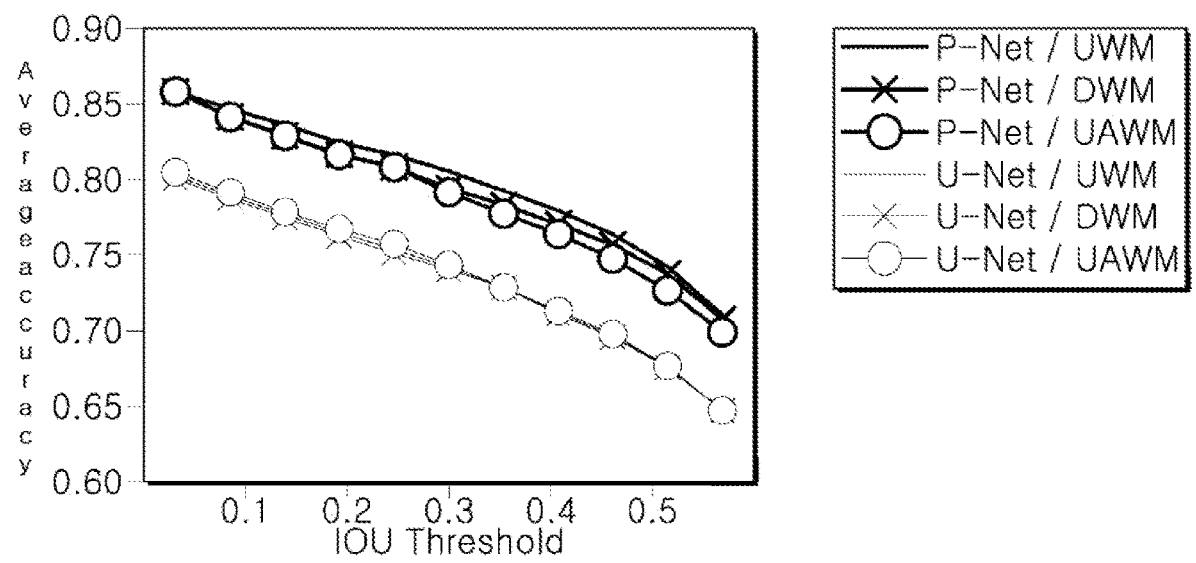

FIGS. 6A to 6C illustrates data that measured accuracy of the classification image 20 created using the existing methods, such as U-Net and UWM (U-Net/UWM), U-Net and DWM (U-Net/DWM), or UAWM and P-Net (UAWM/P-Net) according to an embodiment. FIG. 6A is data of HeLa-U373, FIG. 6B is data of HLA-U, and FIG. 6C is data of HLA-C.

As illustrated in FIG. 6A, the UAWM/P-Net according to an embodiment shows about 33% higher performance in an aspect of accuracy than the U-Net/UWM which is the conventional method. For reference, not shown in the drawings, but the UAWM according to an embodiment shows about 19% higher performance than the conventional UWM (U-Net weight map), and the P-Net learning method according to an embodiment shows about 25% higher performance than the conventional U-Net learning method.

FIGS. 7A to 7G illustrate classification images 20 created using the conventional methods (U-Net/UWM or U-Net/DWM) or the UAWM/P-Net according to an embodiment of the present disclosure.

Referring to FIGS. 7A to 7G, the classification image 20 of the UAWM/P-Net according to the embodiment shows the live cells and the dead cells which are more clearly distinguished than the classification images 20 of the conventional methods (U-Net/UWM, or U-Net/DWM).

Figure 8:
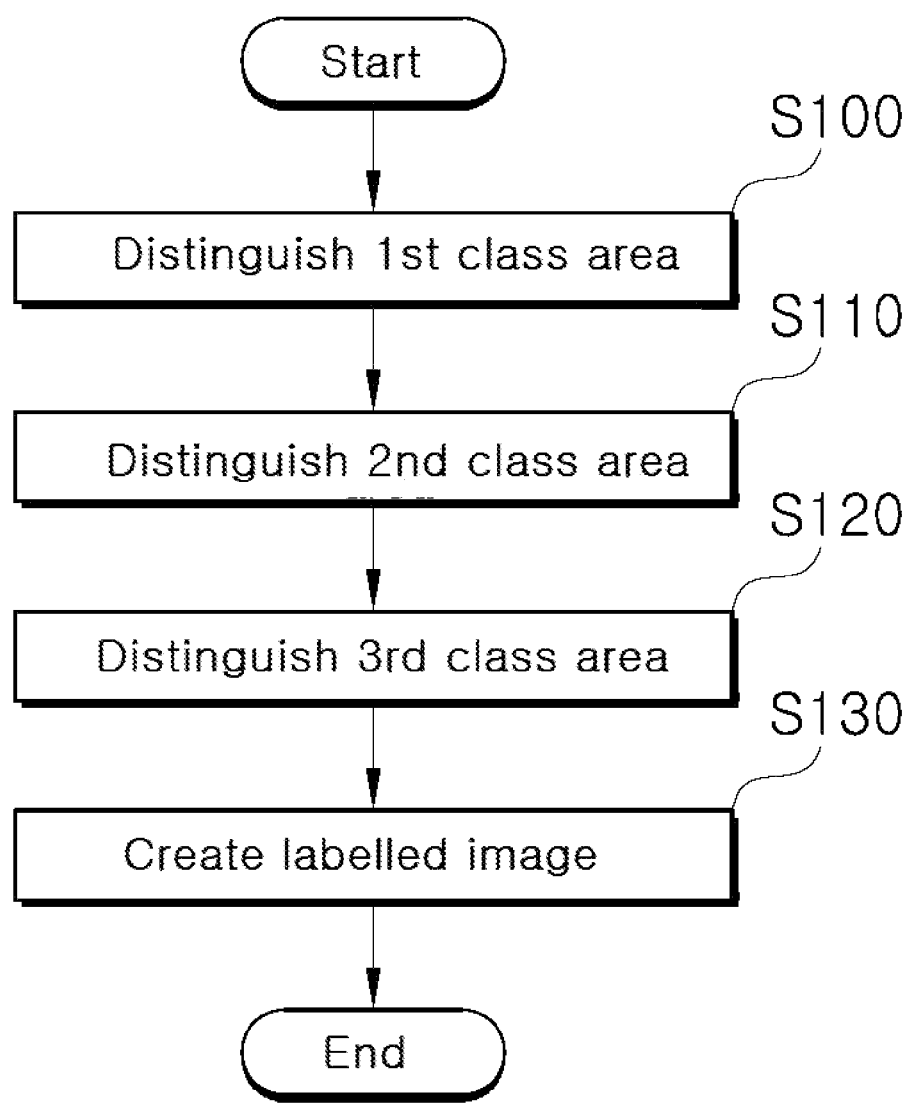
FIG. 8 is a flow chart of a cross-matching image preprocessing method according to an embodiment.

FIG. 8 is a flow chart of a cross-matching image preprocessing method according to an embodiment.

Referring to FIG. 8, the cross-matching image preprocessing method according to the embodiment includes a first class area distinguishing step (S100), a second class area distinguishing step (S110), a third class area distinguishing step (S120), and a labelled image creating step (S130).

First, in the first class area distinguishing step (S100), the preprocessing unit 120 distinguishes the first class area in the original image 10. The first class area is the live cell area, and corresponds to the green color areas in the original image 10, namely, the bright color area in FIG. 3A and the diagonal hatched area in FIG. 3E corresponding to the bright color area.

Additionally, in the second class area distinguishing step (S110), the preprocessing unit 120 distinguishes the second class area in the original image 10. The second class area is the dead cell area, and corresponds to the clear orange color area, namely, the rounded dark color areas in FIG. 3A and the rounded dot-hatched area in FIG. 3E

In addition, in the third class area distinguishing step (S120), the preprocessing unit 120 distinguishes the third class area in the original image 10. The third class area is the background area, and corresponds to an area that the first class area and the second class area are excluded from the original image 10. The background area includes all areas excepting the first class area and the second class area, and includes the lysis cell area, namely, the blur borderline area in FIG. 3A and the dot-hatched area of FIG. 3E corresponding to the blur borderline area.

Moreover, in the labelled image creating step (S130), the preprocessing unit 120 combines the distinguished three class areas, and creates the labelled image. As described above, the labelled image is to express the original image 10 into the three class areas.

Figure 9:
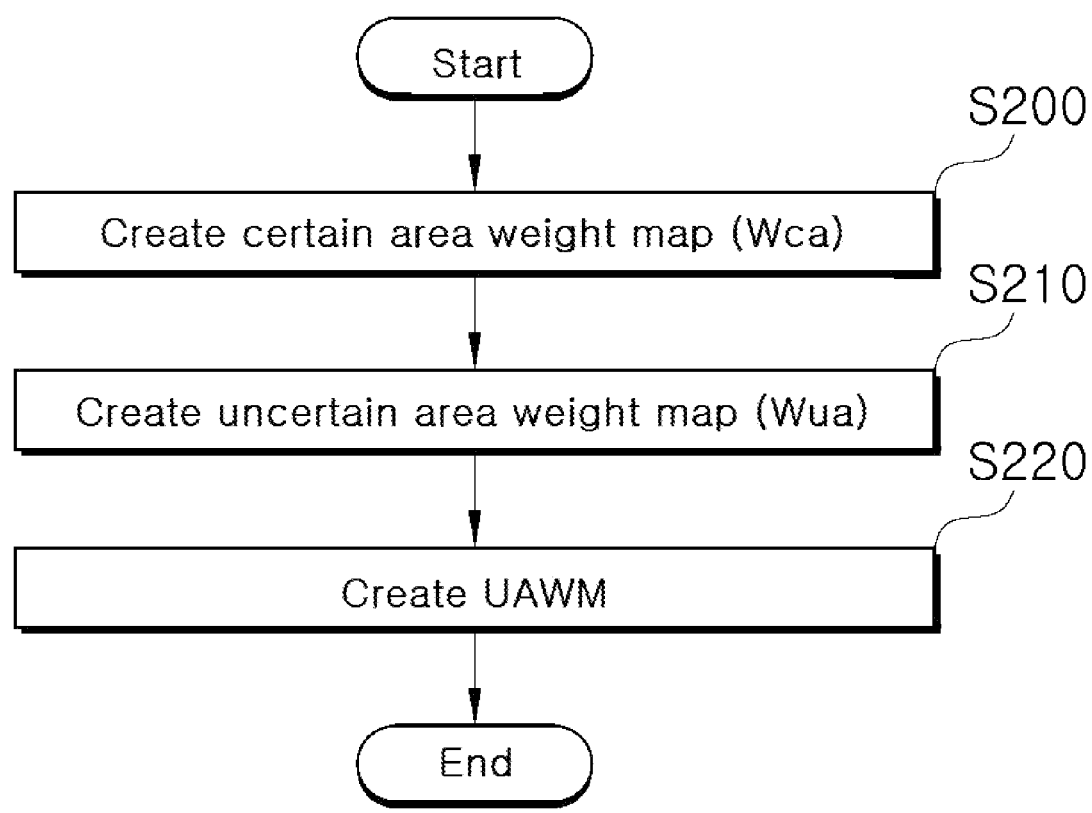
FIG. 9 is a flow chart of an UAWM creating method according to an embodiment.

FIG. 9 is a flow chart of an UAWM creating method according to an embodiment.

Referring to FIG. 9, the UAWM creating method according to the embodiment includes a certain area weight map (Wca) creating step (S200), an uncertain area weight map (Wua) creating step (S210), and an UAWM creating step (S220).

First, in the certain area weight map (Wca) creating step (S200), the UAWM creating unit 130 creates a certain area weight map (Wca) using the labelled image.

As described above, the certain area is a cell inner area which is divided into the live cell area and the dead cell area in the labelled image clearly. The certain area weight map (Wca) is a weight map of the certain area, and has higher weight as an interval between cells gets narrower.

The UAWM creating unit 130 creates the Wca by modeling the certain area in the labelled image.

Furthermore, in the uncertain area weight map (Wua) creating step (S210), the UAWM creating unit 130 creates an uncertain area weight map (Wua) using the labelled image.

As described above, the uncertain area is all remaining areas excluding the certain area in the labelled image. In addition, the Wua is a weight map of the uncertain area, and models influence of the lysis cells included in the uncertain area.

The UAWM creating unit 130 creates the Wua by modeling the uncertain area in the labelled image.

Additionally, in the UAWM creating step (S220), the UAWM creating unit 130 creates an uncertainty-award weight map (UAWM) using the Wca and the Wua.

In detail, the UAWM creating unit 130 weights the Wca and the Wua, and adds up the weighted Wca and the weighted Wua in order to create the UAWM.

Here, a mathematical formula for creating the UAWM using the Wca and the Wua can be expressed as follows:

$$w(x)=\alpha_{ca}w_{ca}(x)+\alpha_{ua}w_{ua}(x)\ s.t.\ \alpha_{ca}+\alpha_{ua}=1 \quad \text{[Mathematical formula 2]}$$

Figure 10:
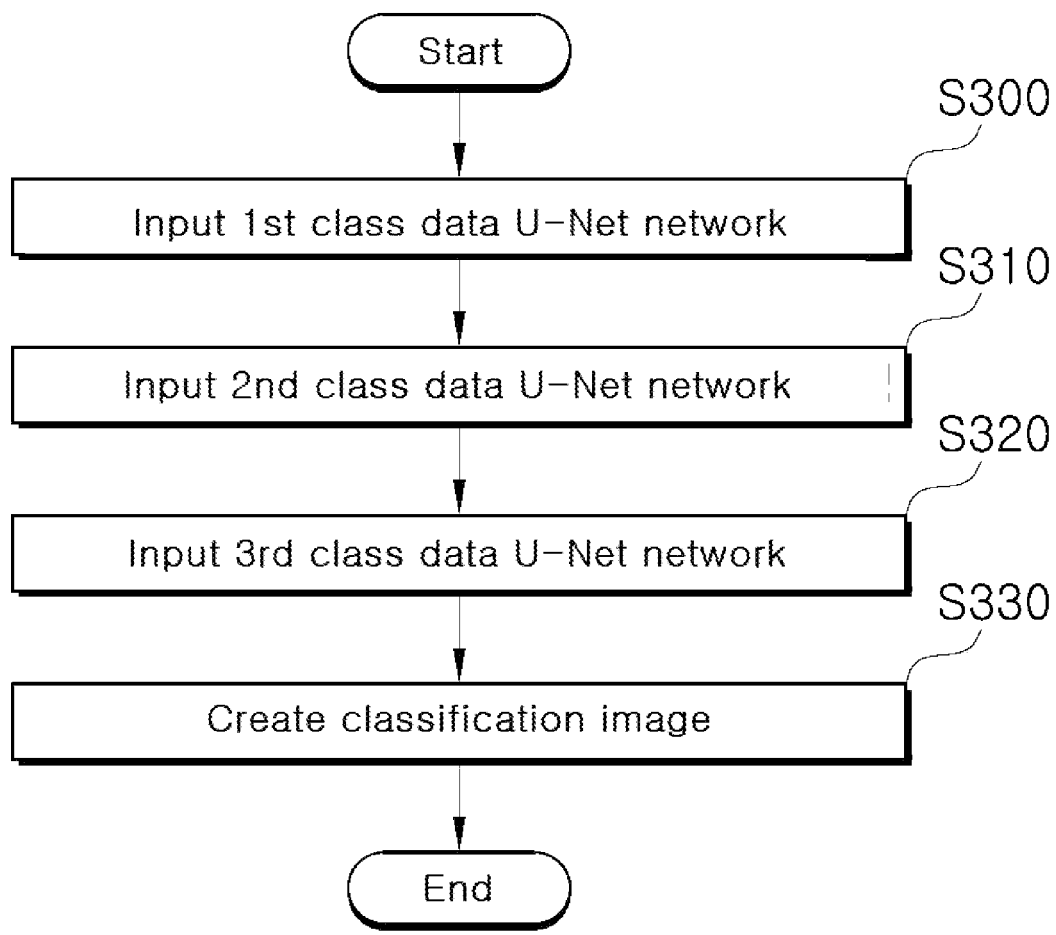
FIG. 10 is a flow chart of a P-Net learning method according to an embodiment.

FIG. 10 is a flow chart of a P-Net learning method according to an embodiment.

Referring to FIG. 10, the P-Net learning method according to the embodiment includes a first class data U-Net network inputting step (S300), a second class data U-Net network inputting step (S310), a third class data U-Net network inputting step (S320), and a classification image creating step (S330).

First, in the first class data U-Net network inputting step (S300), the P-Net learning unit 140 inputs the first class data to the U-Net network, and creates first class classification data which is the U-Net learning result data. The first class data includes at least one among the original image 10, the labelled image in which the first class area is distinguished, and the UAWM.

Next, in the second class data U-Net network inputting step (S310), the P-Net learning unit 140 inputs the second class data to the U-Net network, and creates second class classification data which is the U-Net learning result data. The second class data includes at least one among the original image 10, the labelled image in which the second class area is distinguished, and the UAWM.

Furthermore, in the third class data U-Net network inputting step (S320), the P-Net learning unit 140 inputs the third class data to the U-Net network, and creates third class classification data which is the U-Net learning result data. The third class data includes at least one among the original image 10, the labelled image in which the third class area is distinguished, and the UAWM.

Additionally, in the classification image creating step (S330), the P-Net learning unit 140 fuses at least one among the first class classification data, the second class classification data, and the third class classification data, and creates the classification image 20 which is the P-Net learning result data.

The method for processing cross matching image based on deep learning according to the embodiment is applicable not only to the HLA cross-matching test but also to digital staining, karyotyping, and others.

Figure 11:
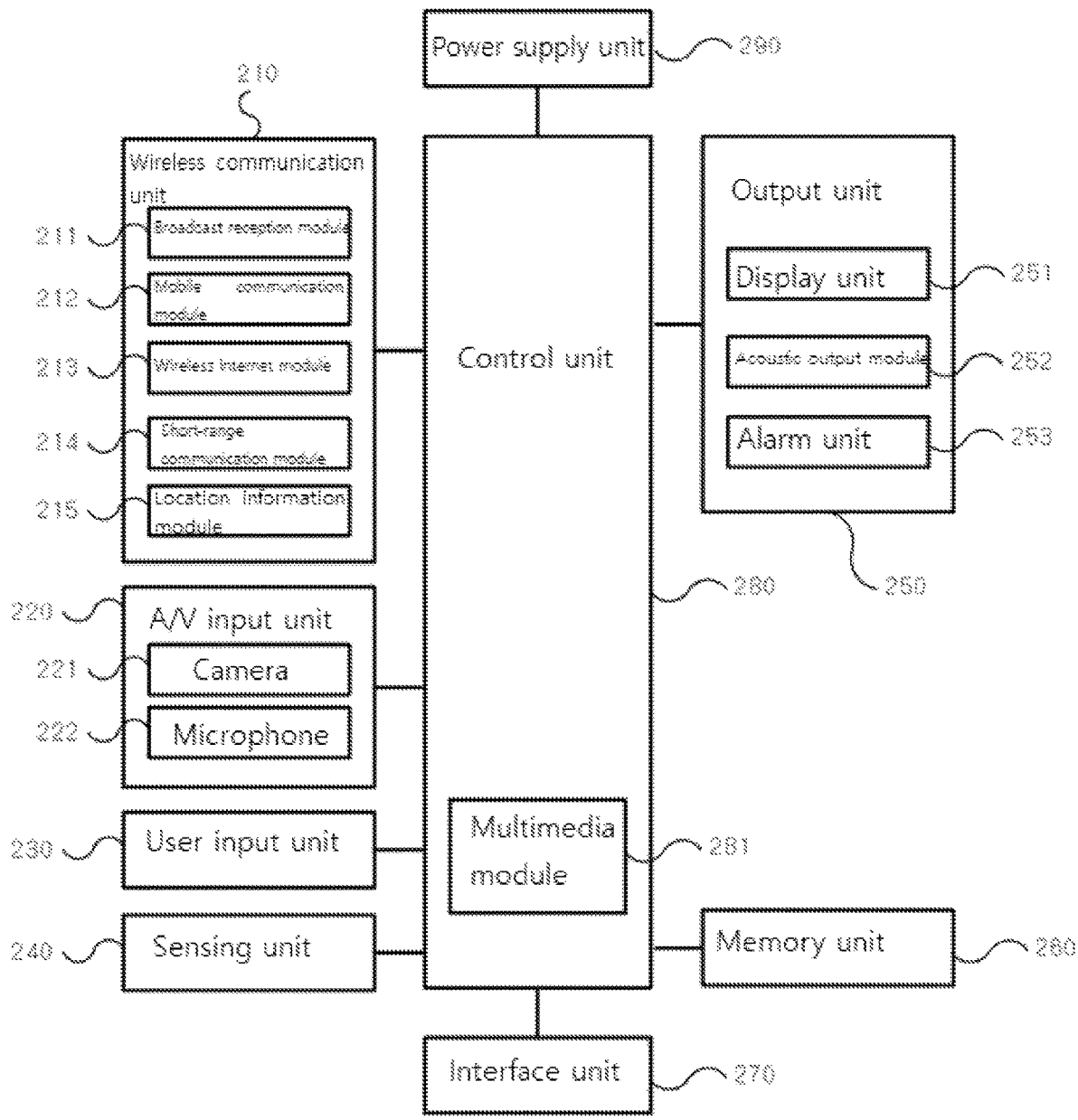
FIG. 11 is a view illustrating the configuration of a user terminal which is an image processing apparatus according to an embodiment.

FIG. 11 is a view illustrating the configuration of a user terminal 200 which is an image processing apparatus 100 according to an embodiment. Hereinafter, component elements of the user terminal 200 illustrated in FIG. 11 will be described.

A wireless communication unit 210 includes one or more elements which performs wireless communication between the user terminal 200 and a wireless communication system or wireless communication between the user terminal 200 and a network where the user terminal 200 is located. For instance, the wireless communication unit 210 may include a broadcast receiver module 211, a mobile communication module 212, a wireless Internet module 213, a short-range communication module 214, and a location information module 215.

The broadcast receiver module 211 receives a broadcast signal or broadcast-related information from an external broadcast management server through a broadcasting channel. Here, the broadcasting channel includes satellite channels, and terrestrial channels. Meanwhile, the broadcast-related information is provided through a mobile communication network, and in this instance, is received by the mobile communication module 212.

Moreover, the mobile communication module 212 sends and receives a wireless signal to and from at least one among a base station, an external terminal, and a server on the mobile communication network. Here, the wireless signal includes data of various types for sending and receiving a voice call signal, a video call signal or a text/multimedia message.

The wireless Internet module 213 is a module for wireless Internet connection, and may be mounted inside or outside the user terminal 200.

The short-range communication module 214 is a module for local area communication. The local area network technology is one of Bluetooth, radio frequency identification (RFID), infrared data association (IrDA), ultra wideband (UWB), ZigBee, and the likes.

Furthermore, the location information module 215 is a module for checking or obtaining a location of the user terminal 200. For instance, the location information module 215 is a global position system (GPS). The GPS module receives location information from a plurality of satellites. Here, the location information includes coordinate information indicated by longitude and latitude.

Meanwhile, an audio/video (A/V) input unit 220 is to input an audio signal or a video signal, and may include a camera 221 and a microphone 222. The camera 221 processes image frames, such as static images or video images, obtained by an image sensor in a video call mode or in a shooting mode. Additionally, the processed image frames are displayed on a display unit 251.

The image frames processed in the camera 221 are stored in a memory 260 or transferred to the outside through the wireless communication unit 210. Two or more cameras 221 may be mounted according to configuration forms of the user terminal 200.

The microphone 222 receives an external sound signal and processes it into an electric voice data in a call mode, in a recording mode, or in a voice recognition mode. Moreover, the processed voice data is converted and output into a form capable of being sent to the mobile communication station through the mobile communication module 212 in the call mode. The microphone 222 can provide various noise elimination algorithms to remove noise generated while external sound signals are input.

A user inputting unit 230 receives input motions from a user, and generates input data for operation control of the user terminal 200.

A sensing unit 240 senses the current states of the user terminal 200, such as location of the user terminal 200, contact with a user, bearing of the user terminal 200, acceleration/deceleration of the user terminal 200, and the likes, and generates a sensing signal to control operation of the user terminal 200.

An interface unit 270 serves as an interface with all external devices connected to the user terminal 200. For instance, the interface unit 270 includes a wired/wireless headset port, an external charger port, a wired/wireless data port, a memory card port, a port for connecting a device having an identity module, an audio input/output (I/O) port, a video input/output (I/O) port, and an earphone port.

An output unit 250 is to output an audio signal, a video signal, or an alarm signal, and includes a display unit 251, an acoustic output module 252, and an alarm unit 253.

The display unit 251 displays and outputs information which is processed in the user terminal 200. For instance, in the call mode, the display unit 251 displays call-related user interface (UI) or graphic user interface (GUI). Furthermore, in the video call mode or in the shooting mode, the display unit 251 displays captured or/and received images or UI or GUI.

Meanwhile, in case of a touch screen that the display unit 251 and a touch pad form a layer structure, the display unit 251 may be used not only as an output device but also as an input device. The display unit 251 may be at least one among a liquid crystal display, a thin film transistor-liquid crystal display, an organic light-emitting diode, a flexible display, and a 3D display. Additionally, two or more display units 251 may be mounted according to configuration forms of the user terminal 200. For instance, the user terminal 200 may include an external display unit (not shown) and an internal display unit (not shown).

The acoustic output module 252 outputs audio data received from the wireless communication unit 210 or stored in the memory 260 in a call signal receiving mode, a call mode, a recording mode, a speech recognition mode, or a broadcast receiving mode. Additionally, the acoustic output module 252 output sound signals relating to functions performed in the user terminal 200, for instance, call signal incoming sound, message incoming sound. Such an acoustic output module 252 includes a speaker, a buzzer, and so on.

The alarm unit 253 outputs a signal for informing event generation of the user terminal 200. Events generated from the terminal are, for example, reception of a call signal, reception of a message, input of a key signal, and so on.

The memory 260 can store programs for processing and controlling the control unit 280 and serve to temporarily store input or output data, for example, phonebooks, messages, static images, or moving images.

The memory 260 includes one or more storage media among a flash memory type memory, a hard disk type memory, a multimedia card micro type memory, a card type memory such as an SD memory or an XD memory, a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk.

The control unit 280 usually controls overall operations of the terminal, and performs control and processing relating to, for instance, voice calls, data communication, and video calls. Moreover, the control unit 280 includes a multimedia module 281 for playing multimedia. The multimedia module 281 may be built in the control unit 280 or may be mounted separately from the control unit 280.

A power supply unit 290 receives an external power supply or an internal power supply by a control of the control unit 280 and supplies power necessary for operations of the components.

An image processing unit 300 performs functions of the image processing apparatus 100 by control of the control unit 280.

The image processing unit 300 performs image processing based on deep learning relative to the received original image 10, and creates a classification image 20. The image processing unit 300 creates the classification image 20 by performing P-Net learning relative to at least one among the original image 10, the labelled image, and the UAWM. That is, the image processing apparatus 100 creates the classification image 20 using the UAWM, which is modeling data of the original image 10, and P-Net learning.

Various embodiments described herein may be implemented in a recording medium readable by a computer or similar device using, for example, software, hardware or a combination thereof.

According to a hardware implementation, the embodiments described herein include application specific integrated circuits (ASICs), digital signal processors (DSPs), digital signal processing devices (DSPDs), programmable logic devices (PLDs), field programmable gate arrays (FPGAs), and the like. It may be implemented using at least one of processors, controllers, microcontrollers, microprocessors, and electrical units for performing other functions. The described embodiments may be implemented by the controller 280 itself.

According to the software implementation, embodiments such as the procedures and functions described herein may be implemented as separate software modules. Each of the software modules may perform one or more functions and operations described herein. Software code may be implemented in software applications written in a suitable programming language. The software code may be stored in the memory 260 and executed by the controller 280.

The embodiments described above may be implemented by hardware components, software components, and/or a combination of hardware components and software components. For example, the devices, methods and components described in the embodiments may be implemented using one or more general purpose or special purpose computers, for example, processors, controllers, central processing units (CPUs), graphic processing units (GPUs), arithmetic logic units (ALUs), digital signal processors, microcomputers, field programmable gate arrays (FPGAs), programmable logic units (PLUs), microprocessors, application specific integrated circuits (ASICs), or any other device capable of executing and responding to instructions.

The method according to the embodiment may be embodied in the form of program instructions that can be executed by various computer means and recorded in a computer readable medium. The computer readable medium may include program instructions, data files, data structures, etc. alone or in combination. The program instructions recorded on the media may be those specially designed and constructed for the purposes of the embodiments, or they may be of the kind well-known and available to those having skill in the computer software arts. Examples of computer-readable recording media include magnetic media such as hard disks, floppy disks, and magnetic tape, optical media such as CD-ROMs, DVDs, and magnetic disks, such as floppy disks. Magneto-optical media, and hardware devices specifically configured to store and execute program instructions, such as ROM, RAM, flash memory, and the like. Examples of program instructions include not only machine code generated by a compiler, but also high-level language code that can be executed by a computer using an interpreter or the like. The hardware device described above may be configured to operate as one or more software modules to perform the operations of the embodiments, and vice versa.

Although the embodiments have been described by the limited embodiments and the drawings as described above, various modifications and variations are possible to those skilled in the art from the above description. For example, the described techniques may be performed in a different order than the described method, and/or components of the described systems, structures, devices, circuits, etc. may be combined or combined in a different form than the described method, or other components. Or even if replaced or substituted by equivalents, an appropriate result can be achieved. Therefore, other implementations, other embodiments, and equivalents to the claims are within the scope of the claims that follow.

The invention claimed is:

1. A method for processing cross matching image based on deep learning, the method comprising:
   a preprocessing operation of combining three class areas distinguished in an original image of a cross-matching test to create a labelled image;
   an operation of modelling a certain area and an uncertain area of the labelled image and creating an uncertainty-aware weight map (UAWM); and
   an operation of creating a classification image in which live cells and dead cells are distinguished in the original image by performing P-Net learning relative to at least one among the original image, the labelled image, and the UAWM.

2. The method of claim 1, wherein the preprocessing operation includes an operation of distinguishing a first class area which is a live cell area, a second class area which is a dead cell area, and a third class area which is a background area in the original image.

3. The method of claim 2, wherein the certain area is a cell inner area which is divided into the live cell area and the dead cell area in the labelled image, and
   wherein the uncertain area is the remaining areas excluding the certain area in the labelled image.

4. The method of claim 3, wherein the UAWM creating operation includes:
   an operation of creating a certain area weight map by modeling the certain area;
   an operation of creating an uncertain area weight map by modeling the uncertain area; and
   an operation of creating the UAWM using the certain area weight map and the uncertain area weight map.

5. The method of claim 4, wherein the UAWM creating operation weights the certain area weight map and the uncertain area weight map, and adds up the weighted certain area weight map and the weighted uncertain area weight map in order to create the UAWM.

6. The method of claim 2, wherein the classification image creating operation inputs data of the first class area, data of the second class area, and data of the third class area to U-Net networks in order to perform P-Net learning.

7. The method of claim 6, wherein the classification image creating operation fuses learning result values of the U-Net networks in order to create the classification image.

8. An apparatus for processing cross matching image based on deep learning, the apparatus comprising:
   a preprocessing unit combining three class areas distinguished in an original image of a cross-matching test to create a labelled image;
   an UAWM creating unit creating an uncertainty-aware weight map (UAWM) by modelling a certain area and an uncertain area of the labelled image; and
   a P-Net learning unit creating a classification image in which live cells and dead cells are distinguished in the original image by performing P-Net learning relative to at least one among the original image, the labelled image, and the UAWM.

9. The apparatus of claim 8, wherein the preprocessing unit distinguishes a first class area which is a live cell area, a second class area which is a dead cell area, and a third class area which is a background area in the original image.

10. The apparatus of claim 9, wherein the certain area is a cell inner area which is divided into the live cell area and the dead cell area in the labelled image, and wherein the uncertain area is the remaining areas excluding the certain area in the labelled image.

11. The apparatus of claim 10, wherein the UAWM creating unit creates a certain area weight map by modeling the certain area, creates an uncertain area weight map by modeling the uncertain area, and creates the UAWM using the certain area weight map and the uncertain area weight map.

12. The apparatus of claim 11, wherein the UAWM creating unit weights the certain area weight map and the uncertain area weight map, and adds up the weighted certain area weight map and the weighted uncertain area weight map in order to create the UAWM.

13. The apparatus of claim 9, wherein the P-Net learning unit inputs data of the first class area, data of the second class area, and data of the third class area to U-Net networks in order to perform P-Net learning.

14. The apparatus of claim 13, wherein the P-Net learning unit fuses learning result values of the U-Net networks in order to create the classification image.

* * * * *